United States Patent [19]
Dudits et al.

[11] Patent Number: 5,545,819
[45] Date of Patent: Aug. 13, 1996

[54] TRANSGENIC PLANTS EXPRESSING A PROKARYOTIC AMMONIUM DEPENDENT ASPARAGINE SYNTHETASE

[75] Inventors: Dénes Dudits; Katalin Paulovics; Katalin Kalman; János Györgyey; Ferenc Nagy; László Bako; Gábor Horvath, all of Szeged, Hungary; Peter Eckes, Kelkheim/Taunus; Günter Donn, Hofheim am Taunus, both of Germany

[73] Assignee: Hoechst Aktiengesellschaft, Frankfurt, Germany

[21] Appl. No.: 360,176

[22] Filed: Dec. 20, 1994

Related U.S. Application Data

[63] Continuation of Ser. No. 238,203, May 4, 1994, abandoned, which is a continuation of Ser. No. 116,045, Sep. 2, 1993, abandoned, which is a continuation of Ser. No. 910,262, filed as PCT/EP91/00120, Jan. 22, 1991 published as WO91/11524, Aug. 8, 1991, abandoned.

[30] Foreign Application Priority Data

Jan. 26, 1990 [EP] European Pat. Off. .............. 90101537

[51] Int. Cl.⁶ .............................. A01H 5/00; A01H 5/10; C12N 15/52; C12N 15/82
[52] U.S. Cl. ..................... 800/205; 800/250; 435/172.3; 435/240.4; 435/320.1; 435/70.1; 536/23.7; 536/24.1; 47/58; 935/64; 935/67
[58] Field of Search ............................ 435/172.1, 172.3, 435/320.1, 240.4, 70.1; 536/23.2, 23.7, 24.1; 800/205, 250; 935/6, 9, 10, 64, 67; 47/58

[56] References Cited

FOREIGN PATENT DOCUMENTS

| 0275957 | 7/1988 | European Pat. Off. . |
| 0303780 | 2/1989 | European Pat. Off. . |
| WO90/13633 | 11/1990 | WIPO . |

OTHER PUBLICATIONS

MGG (1989), Eckes et al., pp. 263–268, "Overproduction of Alfalfa Glutamine Synthetase in Transgenic Tobacco Plants".
Biochem Genetics, vol. 98, 1983, p. 169, "Direct Transfer of the Bacterial Asparagine Synthetase Gene to Mammalian Cells".
Tachibana et al (1986) J Pesticide Sci 11:27–32.
Tachibana et al (1986) J Pesticide Sci 11:33–38.
Weising et al (1988) Ann Rev Genet 22:421–477.
Aota et al (1988) Nucleic Acids Res 16(Supp):r315–r348.
Pai et al (1981) Genetics. Its Concepts and Implications pp. 330–333.
F Salisbury et al (1978) Plant Physiology pp. 192–205.
M Nakamura et al (1981) Nucleic Acids Res 9:4669–4676.
J Watson et al. (1992) Recombinant DNA p. 42.

Primary Examiner—David T. Fox
Assistant Examiner—Bruce R. Campell
Attorney, Agent, or Firm—Curtis, Morris & Safford, P.C.

[57] ABSTRACT

The gene asnA which encodes a prokaryotic ammonium-specific asparagine synthetase (ASN-A) can be introduced into plant cells. Such transformed cells and plants developed therefrom not only tolerate glutamine synthetase inhibitors but are effectively stimulated by such herbicides.

24 Claims, 5 Drawing Sheets

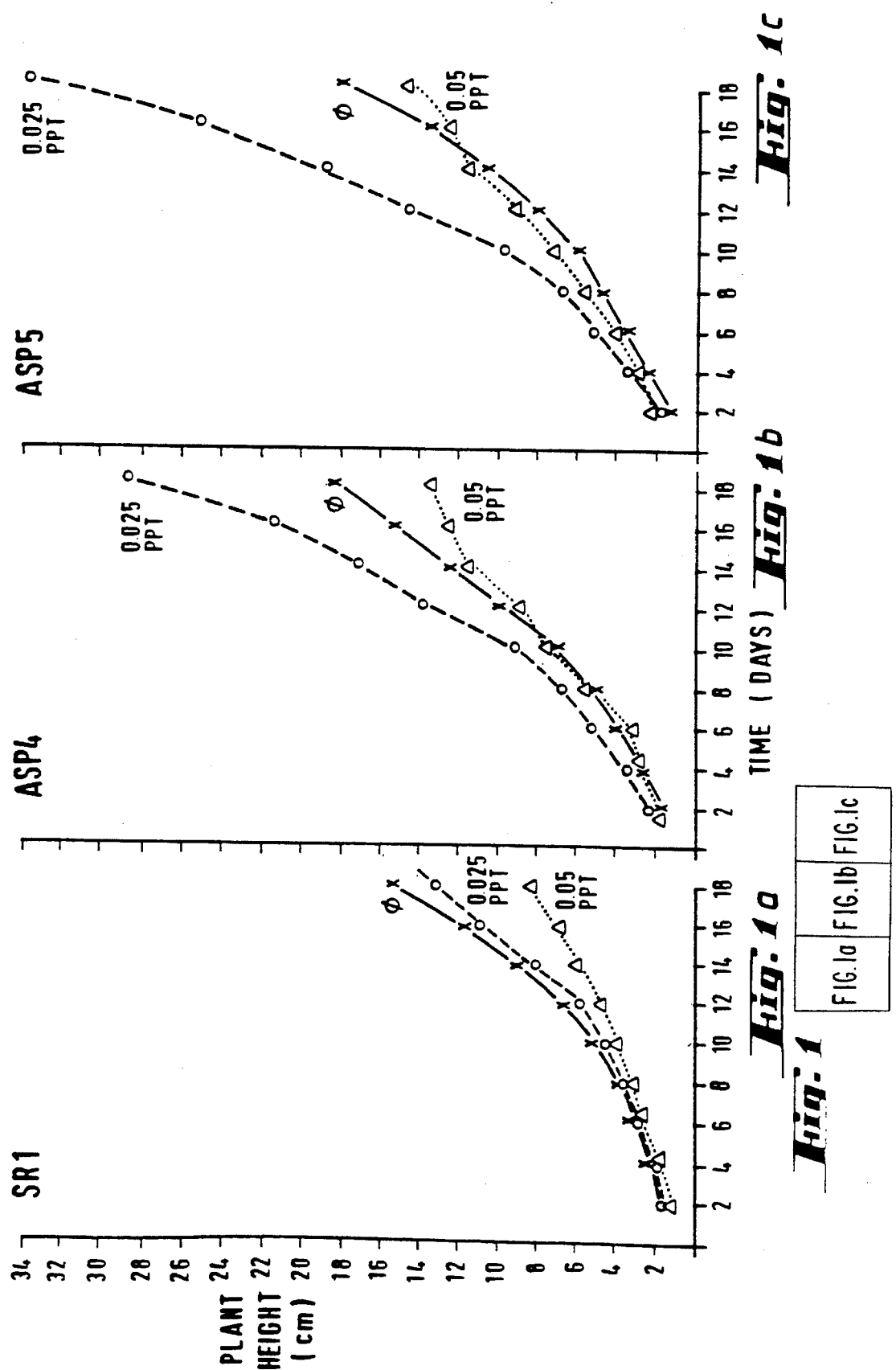

ved as WO91/11524, Aug. 8, 1991, now abandoned.

TRANSGENIC PLANTS EXPRESSING A PROKARYOTIC AMMONIUM DEPENDENT ASPARAGINE SYNTHETASE

This application is a continuation of application Ser. No. 08/238,203, filed May 4, 1994, now abandoned which is a continuation of Ser. No. 08/116,045, filed Sep. 2, 1993, now abandoned which is a continuation of application Ser. No. 07/910,262, filed as PCT/EP91/00120, Jan. 22, 1991 published as WO91/11524, Aug. 8, 1991, now abandoned.

FIELD OF THE INVENTION

The invention relates to transgenic plants expressing a prokaryotic ammonium dependent asparagine synthetase.

BACKGROUND OF THE INVENTION

Asparagine plays an important role as a transport form of nitrogen and in many plants—including nitrogen fixers—it is the principle compound involved in the transfer of nitrogen from the roots into the transpiration stream. In plants asparagine is formed from glutamine, aspartate and ATP catalyzed by the asparagine synthetase ASN (E.C. 6.3.5.4 ) whereby glutamate, AMP and pyrophosphate are formed as by-products.

SUMMARY OF THE INVENTION

It now has been found that the prokaryotic, ammonium dependent asparagine synthetase ASN-A (E. C. 6.3.1.1) can be introduced into plant cells, resulting in transgenic plants which show a number of advantages: The plants show a more efficient net photosynthetic $CO_2$-fixation, an increased growth rate, accelerated plant development, earlier flower formation, increased green mass and plant dry weight. Thus, the growth area can be extended to regions with a less favourable climate and in regions with a warm climate e.g. three instead of two crops are possible. Furthermore, the transgenic plants tolerate the application of glutamine synthetase (GS) inhibitors, e.g. phosphinothricine (PPT) or methionine sulfoximine (MSX) and even show a stimulation of photosynthesis and growth upon application of such inhibitors.

BRIEF DESCRIPTION OF DRAWINGS

FIGS. 1a–1c show basic as well as PPT induced acceleration in growth by various curves (time (days) vs. plant height (cm); SR1, ASP4, ASP5);

DETAILED DESCRIPTION

Figure 2A:
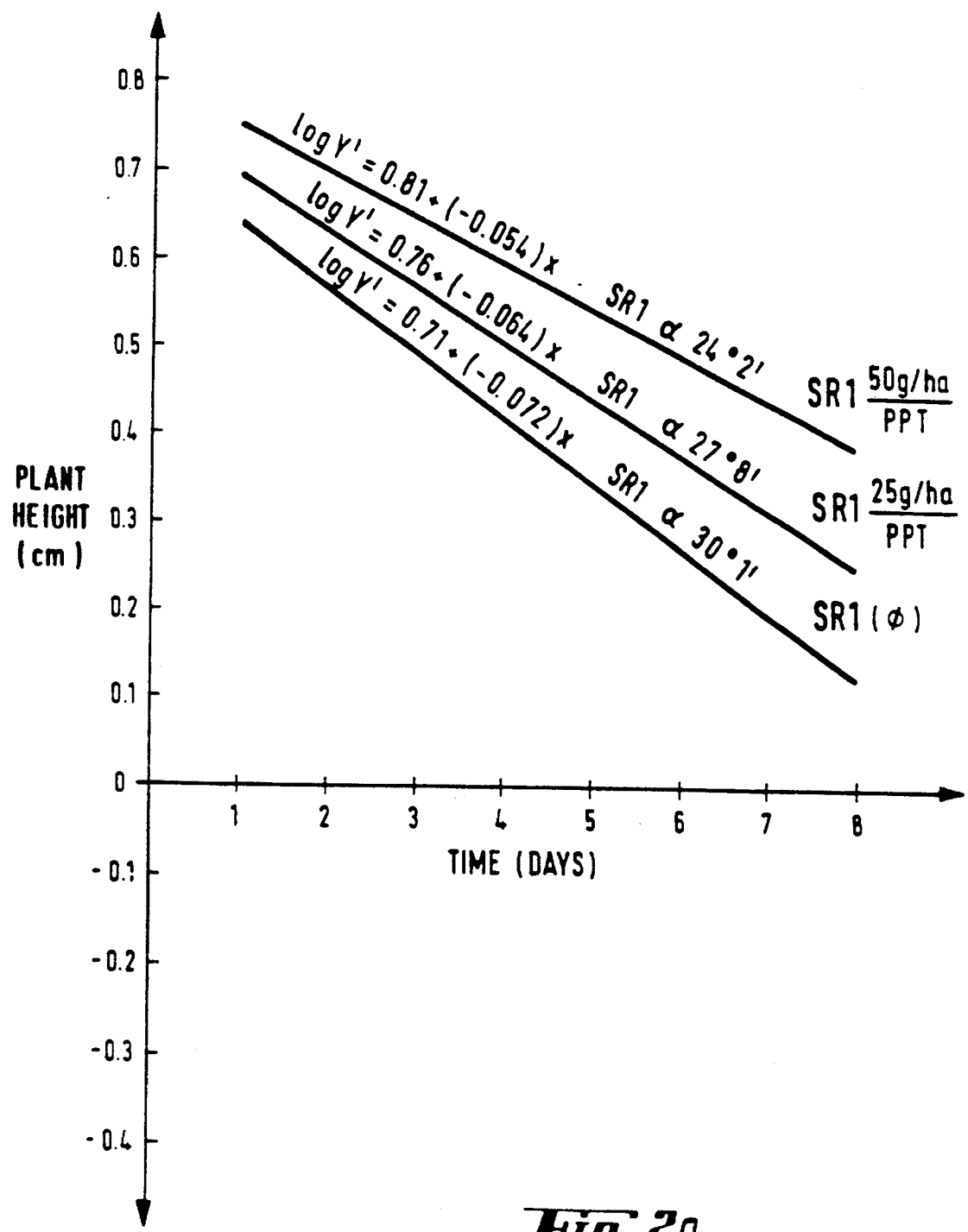
FIGS. 2a–2c show the difference between various lines under control and treated conditions by characterizing growth by Baule Mitscherlich-curves; and, FIG. 3 shows Baule-Mitscherlich curves demonstrating that ASP plants exhibit faster growth thn control SR1 plants grown in the field.

In contrast to the ASN encoding gene (or genes) of higher plants (asn gene) the asnA gene of E. coli codes for a different type of ASN which uses ammonium rather than glutamine for the production of asparagine (Cedar and Schwartz (1969) J. Biol. Chem. 244, 4112–4121). The gene for this enzyme has been isolated and characterized by Nakamura et al. (1981) Nucleic Acids Research 9, 4669–4676. It was found that this prokaryotic enzyme is active in plants and it opens a new ammonium assimilation pathway in these transgenic plants. It results in an overall change of the plant nitrogen metabolism with a stimulatory effect on growth and green mass production.

Under normal conditions in the transformants both GS and ASN-A use ammonia. The advantage of the bacterial pathway will be more pronounced during darkness when the chloroplast GS activity is limited by the reduced availability of ATP, energy charge and magnesium ions (O'Neal and Joy (1974) Plant Phys. 54, 773–779; Joy (1988) Can. J. Bot. 66, 2103–2109). Moreover, the expression of the bacterial asn-A gene in plants even allows an assimilation of ammonia when the plant GS is blocked by specific inhibitors like PPT. In non-transformed plants the inhibition of GS activity disturbs the main road of ammonia utilization and the accumulation of ammonium is one of the key factors in lethality of the treated plants (Tachibana et al. (1986) J. Pesticide Sci. 11, 33–37). Thus the presence of the bacterial enzyme can reduce the ammonia accumulation in PPT-treated transgenic plants which so not only can survive doses of herbicides which are lethal for wild-type plants but rather the so treated transgenic plant shows growth stimulation.

It is apparent for a skilled person that these positive effects are not limited to the asnA gene from E. coli since other bacteria contain the same gene or a gene having the same capability of amidating asparaginic acid and its salts to yield asparagine.

Thus the invention relates to the use of a prokaryotic asnA gene in a plant cell, a gene construct comprising a gene encoding a prokaryotic asnA, operatively linked to a regulatory sequence which effects the expression of the said gene in a plant cell, a vector containing such a gene construct, a plant cell transformed with such a gene construct or vector and expressing a prokaryotic ammonia specific asparagine synthetase in a plant, especially a crop plant, and seeds or propagation material of such plants which contain transformed cells as hereinbefore defined.

Preferred embodiments comprise the use of the E. coli asnA gene encoding the said enzyme and synthetic genes encoding the said enzyme, especially genes comprising codons which are preferably used by plants. The invention also comprises genes which encode enzymes having a different amino acid composition than the natural enzymes but with essentially the same catalytic activity by deleting or adding codons or by replacing codons in the natural genes by such which encode a different amino acid. All such modifications are within the ordinary skill of persons involved in this art.

EXAMPLES

Example I

Figure 3:
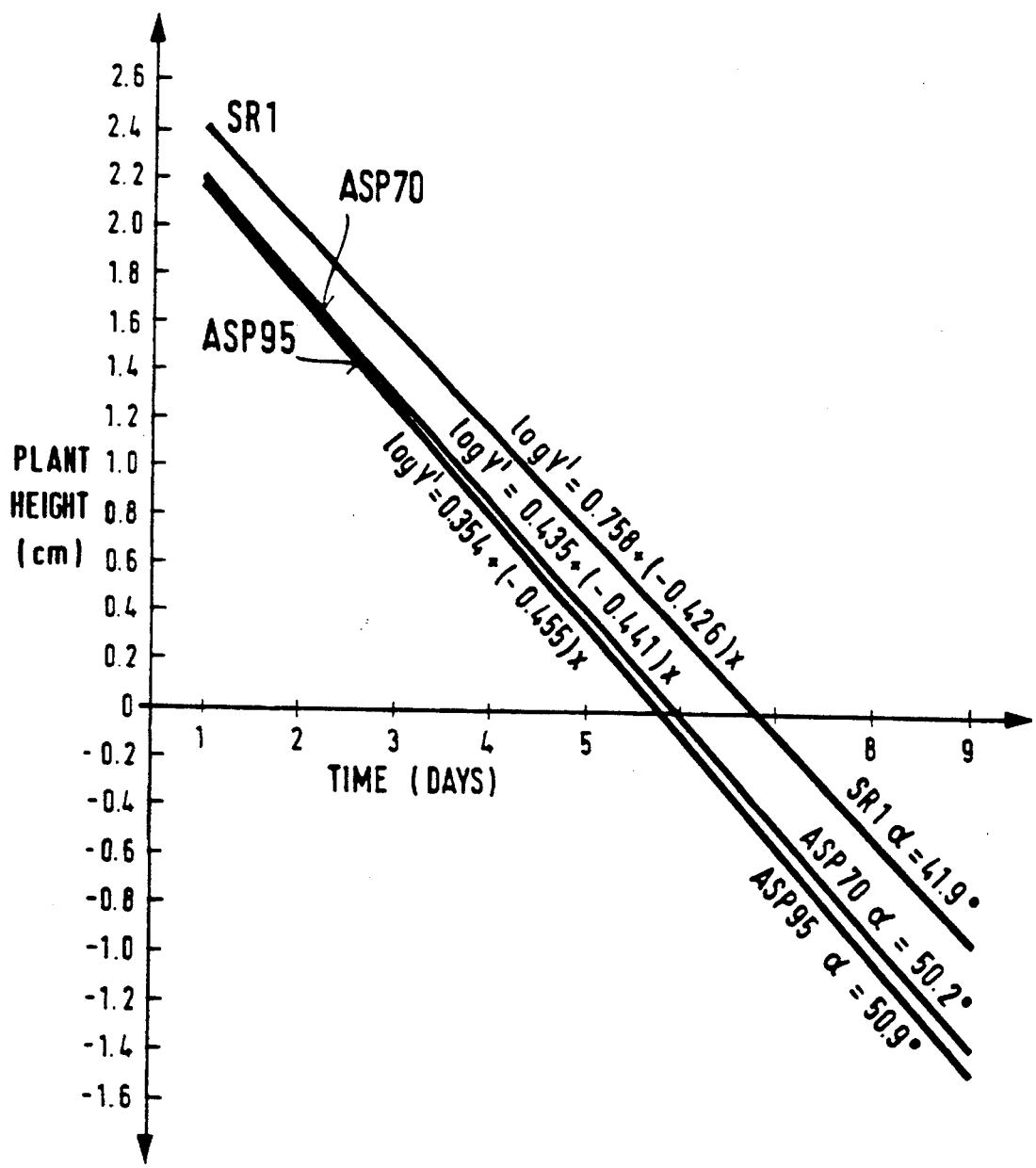

Expression of the E. coli asnA gene with the RUBISCO small subunit promoter in tobacco 1. Production of transgenic tobacco plants Based on the complete nucleotide sequence of the asnA gene from E. coli (Nakamura et al., (1981) Nucleic Acids Research 18, 4673, FIG. 3) we recloned the PstI-HgaI fragment from the plasmid pMY114 into pUC9. Then the asnA gene (1.1 kb) was linked to the promoter of the small subunit gene for pea ribulose 1,5-bisphosphate carboxylase ("RUBISCO", Herrera-Estrella et al. (1984) Nature 310, 115–120) and the whole fragment was introduced into the Agrobacterium vector pPCV001 (Koncz and Schell (1986) Mol. Gen. Genet. 204, 383–396). After leaf disc transformation of SRI tobacco plants the transgenic plants were identified on the basis of their kanamycin resistance. Among several transformants we selected two plants (ASP4, ASP5) which showed tolerance against treatment with 1 kg/ha PPT. As result of this PPT treatment the SR1 control plants were completely killed and we could never find outgrowings with a capability for flowering and seed production. The ASP4 and ASP5 transformants showed symptoms only on the lower and older leaves while the meristematic region could overcome the inhibition. After continuation of growth these plants flowered and produced seeds.

Selfing the ASP4 and ASP5 transgenic tobacco plants has resulted in a segregating seedling population with resistant and sensitive sexual progenies. Under the in vitro conditions used the presence of 10 μM L-PPT in the culture medium could clearly discriminate between the two phenotypes.

The presence of the asnA sequence in the genome of the transformants was also shown by Southern DNA hybridization. After digestion of plant DNAs with EcoRI a hybridizing fragment was revealed in the transformed plants. In Northern hybridization analysis, a low amount of mRNA which was homologous to the asnA gene was detected in the total RNA isolated from the in vitro grown ASP5 transformant.

2. Reduced ammonia accumulation in transgenic tobacco plants

The inhibition of GS activity by PPT treatment causes a rapid increase in ammonia concentration in leaves of control tobacco plants. The rate of ammonia accumulation measured with the microdiffusion method and subsequent nesslerization (Shelp et al. (1985) Can. J. Bot. 63, 1135–1140) depends on the concentration of the applied herbicide.

At a dose of 0.5 kg/ha the transgenic plants can overcome the effects of PPT treatment (Tab. 1).

TABLE 1

Accumulation of ammonia in control tobacco plants (SR1) and in transgenic plants with the asnA gene after spraying with 0.5 kg/ha PPT

| | ammonia concentration (mM) | | |
|---|---|---|---|
| hours | SR1 | ASP4 | ASP5 |
| up to 4 | 0.58 | 0.42 | 0.40 |
| 6 | 1.20 | 0.82 | 0.78 |
| 24 | 1.70 | 0.70 | 0.75 |
| 48 | 1.95 | 0.60 | 0.50 |

A reduced level of accumulation can also be seen in these plants in comparison to SR1 tobacco plants after spraying with 1 kg/ha (Tab. 2). The detected lower ammonia level will be responsible for the less pronounced damage of transformed plants.

TABLE 2

Effects of 1 kg/ha PPT on ammonia concentration in tobacco (SR1) and transgenic plants (ASP4, ASP5)

| | ammonia concentration (mM) | | |
|---|---|---|---|
| hours | SR1 | ASP4 | ASP5 |
| up to 6 | 0.8 | 0.78 | 0.88 |
| 8 | 2.2 | 0.87 | 0.95 |
| 24 | 4.9 | 2.0 | 1.40 |
| 48 | 8.6 | 4.1 | 3.6 |

3. Stimulation of plant growth and development

Detailed comparison of growth behaviour between control and ASP plants revealed considerable differences: An increased growth rate was characteristic for the transgenic plants but a more significant stimulation was achieved by treatment of ASP plants with low doses of PPT.

The basic as well as the PPT induced acceleration in growth could be demonstrated by various types of growth curves. FIG. 1 shows that while the spraying with 0.025 kg/ha PPT already inhibited the growth of SR1 plants a large stimulation was detected in both of the transformants. Spraying with 0.05 kg/ha PPT has a negative influence on all plants. Each point represents the average height of three plants.

Figure 2B:
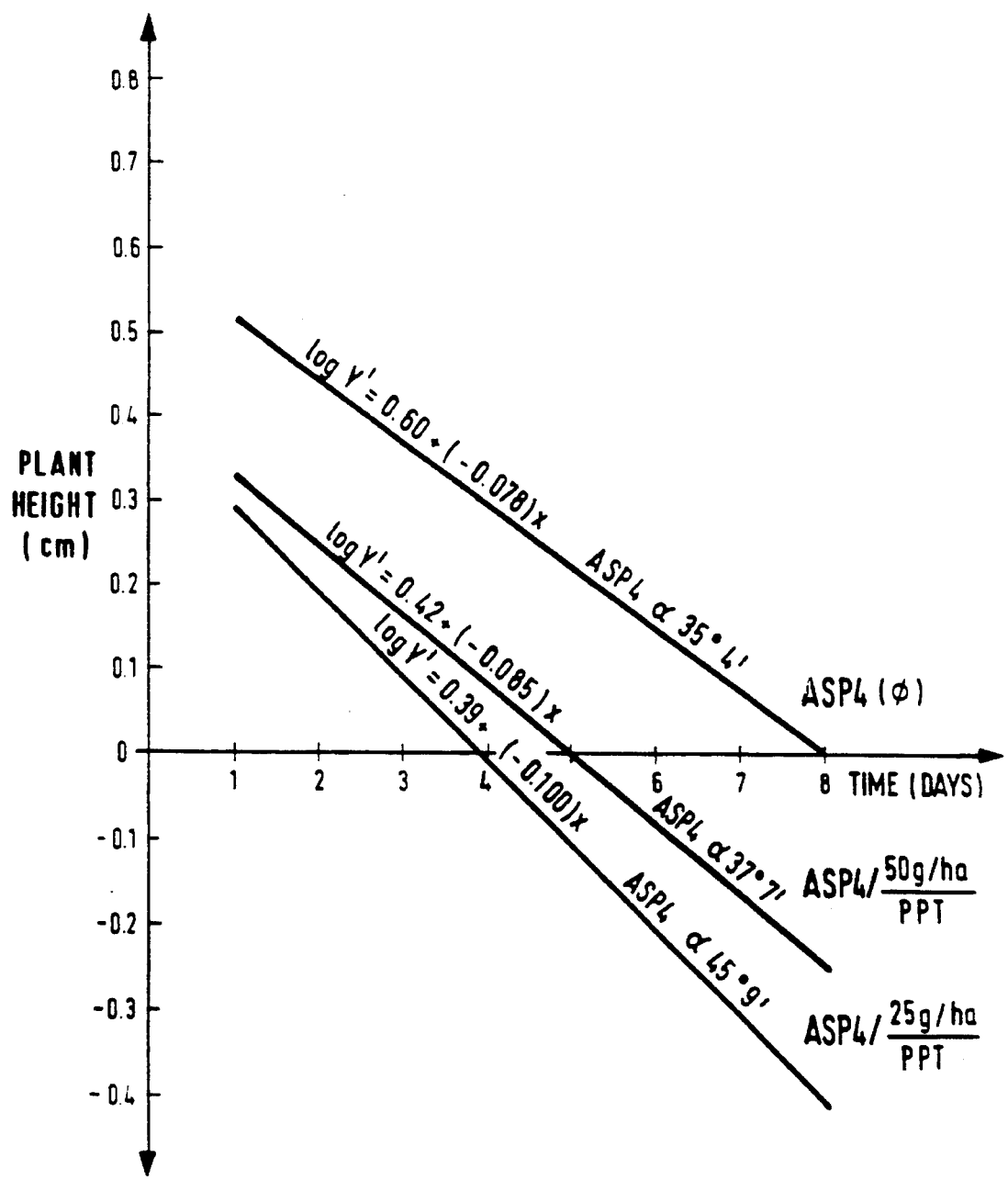
Figure 2C:
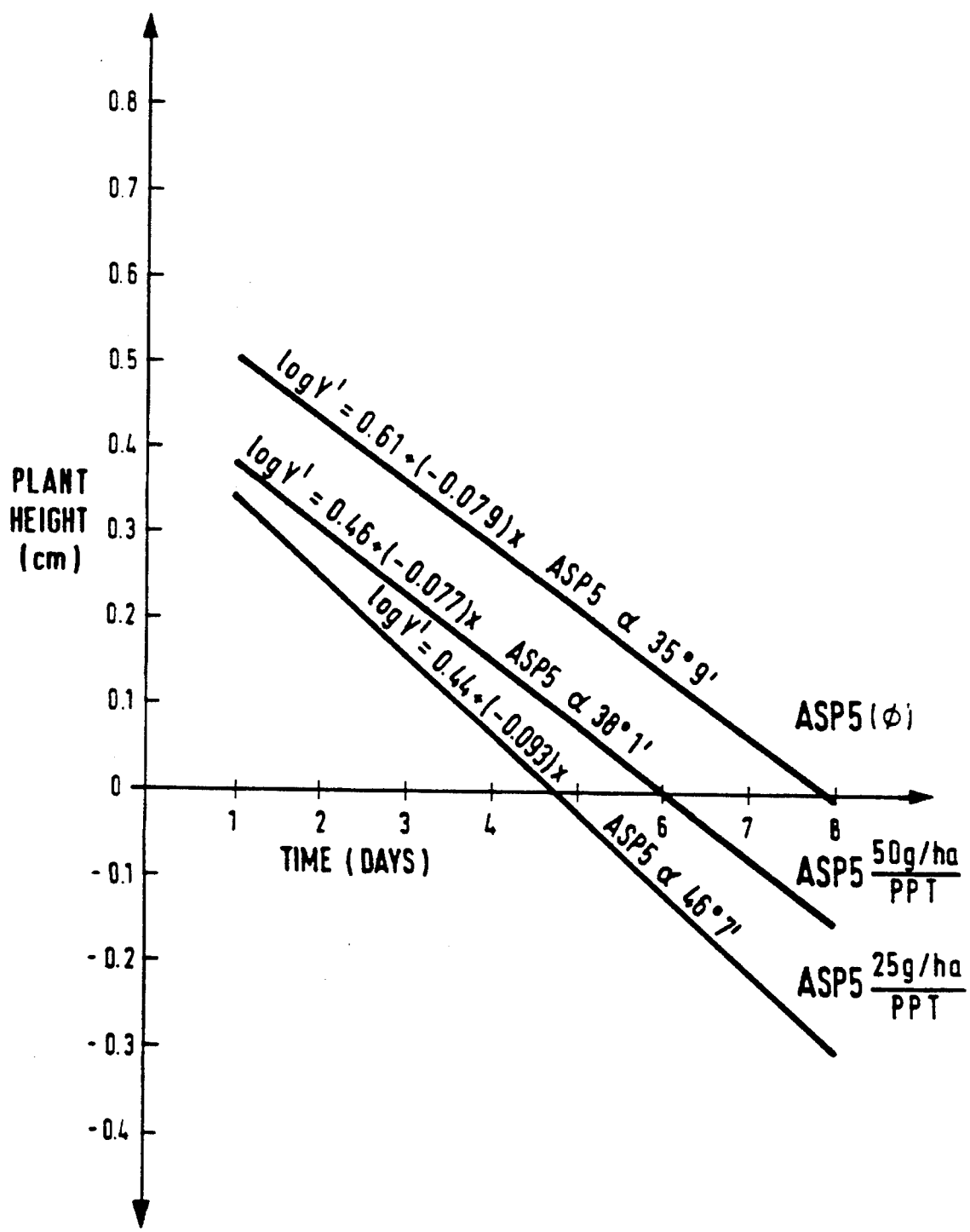

The differences between the various lines under control and treated conditions are also detectable if we characterize the growth of plants by Baule Mitscherlich-curves (FIG. 2) under greenhouse conditions. The inhibition and stimulation of growth can be followed by the slope of plots with characteristic alpha angles shown in FIG. 2.

4. Increased dry weight in transgenic plants

In addition to the differences in plant height the stimulatory effects were also detectable by measuring dry weight. The data shown in Table 3 demonstrate the higher productivity of the asnA transformants:

TABLE 3

Final dry weight (gr) of control (SR1) and transformants (ASP4, ASP5)

| | Treatment | | | |
|---|---|---|---|---|
| Lines | Control | | 0.025 kg/ha PPT | |
| SR1 | 3.19 | 100% | 2.76 | 100% |
| ASP4 | 3.85 | 120% | 4.79 | 173% |
| ASP5 | 3.74 | 117% | 5.05 | 183% |

Example II

Effect of the asnA gene driven by the CaMV35S promoter in transgenic plants

1. Selection of transgenic plants

As an alternative approach we have introduced plasmid molecules (pUC) carrying the E. coli asnA gene with the CaMV35S promoter into SR1 leaf protoplasts by direct DNA uptake (R. X. Fang et al. (1989) The Plant Cell 1, 141–150). The transformants were directly selected on the basis of their PPT resistance. Plants were regenerated from micro calli grown in the presence of 10 μM L-PPT. The Southern hybridization confirmed the presence of the asnA gene in DNA isolated from the PPT resistant regenerants.

2. Reduced ammonia accumulation and improved PPT tolerance in transgenic plants

Selfing of regenerated transformants resulted in segregating progenies with various levels of PPT resistance (medium supplemented with up to 30 μM L-PPT). In agreement with the resistant phenotype the transformed plants accumulate less ammonia than the SR1 plants when sprayed with 1 kg/ha PPT (Tab. 4).

TABLE 4

Ammonia accumulation after spraying the plants with 1 kg/ha PPT

| | ammonia concentration (mM) | | |
|---|---|---|---|
| hours | SR1 | ASP70 | ASP95 |
| 6 | 6.85 | 2.92 | 1.95 |
| 24 | 9.50 | 5.60 | 5.10 |

TABLE 4-continued

Ammonia accumulation after spraying the plants with 1 kg/ha PPT

| hours | ammonia concentration (mM) | | |
|---|---|---|---|
| | SR1 | ASP70 | ASP95 |
| 48 | 22.3 | 13.60 | 17.40 |
| 120 | 58.60 | 28.30 | 35.6 |
| 144 | 113.00 | 39.40 | 50.00 |

3. Efficiency of photosynthesis

Both the control SR1 and transgenic tobacco plants were characterized by various parameters of photosynthesis such as the $CO_2$ fixation rate (Szajko et al. 1971, Acta Agr. Acad. Hung. 20, 247–260) and fluorescence induction (Hideg et al., 1986, Photobiochem. Photobiophys. 12, 221–230). Under greenhouse conditions the plants were treated with various doses of PPT and the content of ammonium was also determined. As shown by Table 5 the transgenic plants with the ASN-A gene exhibit a considerable increase in efficiency of net $CO_2$ fixation in comparison to the control plants. Application of low dose PPT treatment can further stimulate $CO_2$ fixation, while the difference between SR1 plants with or without PPT (50 g/ha) treatment is not statistically significant. The Table 5 provides also evidence that in the case of tobacco plants the inhibitory concentration of PPT causes ammonium-accumulation with serious damage in photosynthesis by inhibition of electron transport and a 50% reduction of $CO_2$ fixation. Under the same conditions the transformed plants (ASP 70) can tolerate the treatment as the photosynthetic function is concerned.

4. Growth behaviour of asnA transformant plants

Analysis of growth rate (mm/day) reproducibly showed accelerated growth of transformants during the early plant development. Data are shown in Table 6 for plants grown in the green house.

TABLE 5

| | | | Parameters of photosynthesis | | | | | | |
|---|---|---|---|---|---|---|---|---|---|
| | PPT treatment | Ammonia concentration | $CO_2$ fixation ($\mu$mol $CO_2$/dm$^2$xh) | | | | Fluorescence induction (in % of control SR1) | | |
| Lines | (g/ha) | (mM) | $\bar{x}$ | $\pm s_{\bar{x}}$ | n | P 1% | $F_m$ | $F_o$ | $F_i - F_o/F_m - F_o$ |
| SR1 | 0 | 0.37 | 38.17 | 12.05 | 20 | — | 100 | 100 | 0.45 |
| | 50 | 2.00 | 44.23 | 17.73 | 20 | — | 101 | 102 | 0.44 |
| | 750 | 34.35 | 19.54 | 12.42 | 20 | + | 80 | 194 | 0.59 |
| ASP70 | 0 | 0.47 | 49.32 | 7.86 | 20 | + | 98 | 114 | 0.38 |
| | 50 | 2.70 | 58.07 | 6.06 | 20 | + | 99 | 110 | 0.42 |
| | 750 | 15.80 | 31.61 | 14.16 | 20 | — | 92 | 144 | 0.49 |

The analysis was carried out 4 days after PPT treatment.

TABLE 6

| | Growth rate (mm/day) during various periods of plant development (green house) | | | | | | | | | |
|---|---|---|---|---|---|---|---|---|---|---|
| | Periods (6 days) | | | | | | | | Final plant height | |
| Lines | I | II | III | IV | V | VI | VIII | VIII | (cm) | |
| SR1 | 0.29 | 0.45 | 0.27 | 0.52 | 0.75 | 1.31 | 1.93 | 1.37 | 41.08 | |
| Asp70/1 | 0.60 | 1.15 | 0.43 | 1.23 | 1.83 | 2.08 | 1.53 | 0.50 | 58.0 | 141% |
| Asp70/2 | 0.61 | 0.93 | 0.50 | 0.75 | 1.18 | 1.51 | 1.83 | 0.25 | 48.5 | 118% |

SR1: average of 5 plants
ASP70/1 and ASP70/2: individual plants

The analysis of these plants under field conditions revealed similar differences as it was observed in the green house (Table 7). The growth rate of ASP plants during period I–III was considerably higher than in the case of SR1 plants. In this experiment the stimulatory effect of PPT on the transgenic plants was also confirmed especially in the last growing period. The Baule-Mitscherlich curves (FIG. 3) clearly demonstrate that the ASP plants exhibit faster growth than control SR1 plants grown in the field.

TABLE 7

Growth rate (mm/day) during various periods of plant development (field experiment)

| Treatment | Lines | Periods (7 days) | | | | Final plant height (cm) | |
|---|---|---|---|---|---|---|---|
| | | I | II | III | IV | | |
| Control | SR1 | 0.36 | 0.85 | 1.31 | 3.24 | 42.5 | 100% |
| | Asp70 | 0.45 | 1.07 | 1.50 | 3.14 | 47.6 | 112% |
| | Asp95 | 0.48 | 1.14 | 1.92 | 3.24 | 51.5 | 121% |
| 25 g/ha PPT | SR1 | 0.29 | 0.56 | 1.15 | 2.74 | 35.0 | 100% |
| | Asp70 | 0.44 | 1.02 | 1.69 | 3.84 | 53.8 | 154% |
| | Asp95 | 0.31 | 0.88 | 1.27 | 3.78 | 48.7 | 139% |

Average of 5 plants

5. Productivity of asnA transformants

As shown by Table 8 the total green mass as well as the dry weight was increased in ASP plants in comparison to SR1 plants. Here we can also see that the transgenic plants are significantly stimulated by PPT treatment. At the same time the control SR1 plants are already inhibited by the spraying.

TABLE 8

| Lines | Control | | | | 25 g/ha PPT | | | |
|---|---|---|---|---|---|---|---|---|
| | Total | % | Leaf | % | Total | % | Leaf | % |
| Green mass (gr) field test | | | | | | | | |
| SR1 | 86.5 | 100 | 57.4 | 100 | 78.7 | 100 | 43.4 | 100 |
| ASP70 | 95.2 | 110 | 62.3 | 108 | 139.9 | 178 | 92.41 | 213 |
| ASP95 | 103.8 | 120 | 68.4 | 119 | 105.0 | 133 | 71.56 | 165 |
| Dry weight (gr) field test | | | | | | | | |
| SR1 | 6.66 | 100 | 4.83 | 100 | 6.42 | 100 | 5.05 | 100 |
| ASP70 | 8.05 | 121 | 5.82 | 120 | 10.99 | 171 | 8.56 | 169 |
| ASP95 | 8.48 | 127 | 6.34 | 131 | 8.96 | 140 | 6.78 | 134 |

All average data from 5 plants

We claim:

1. A plant cell containing DNA coding for *E. coli* ammonium-specific asparagine synthetase, type A, wherein the cell expresses *E. coli* ammonium-specific asparagine synthetase, type A.

2. A plant containing cells as claimed in claim 1.

3. A gene construct comprising a first nucleotide sequence consisting of DNA encoding an *E. coli* ammonium-specific asparagine synthetase, type A, operatively linked to a second nucleotide sequence consisting of DNA encoding a regulatory sequence which effects expression of said first nucleotide sequence in a plant cell.

4. A gene construct according to claim 3 wherein the second nucleotide sequence is a plant promoter.

5. A gene construct according to claim 4 wherein the second nucleotide sequence is the promoter of the small subunit gene for pea ribulose 1,5-bisphosphate carboxylase.

6. A vector containing a gene construct according to claims 3, 4, or 5.

7. A plant cell containing DNA coding for *E. coli* ammonium-specific asparagine synthetase, type A, wherein the cell expresses *E. coli* ammonium-specific asparagine synthetase, type A, by containing a gene construct according to claims 3, 4, or 5.

8. A plant cell containing DNA coding for *E. coli* ammonium-specific asparagine synthetase, type A, wherein the cell expresses *E. coli* ammonium-specific asparagine synthetase, type A, by containing a vector according to claim 6.

9. The plant cell of claim 8 wherein the vector is an Agrobacterium vector.

10. A seed containing cells as claimed in claim 1.

11. A plant containing cells as claimed in claim 7.

12. A seed containing cells as claimed in claim 7.

13. A method for increasing growth of a plant comprising: transforming a plant cell with a vector as claimed in claim 7 so that the cell contains DNA coding for *E. coli* ammonium-specific asparagine synthetase, type A, wherein the cell expresses *E. coli* ammonium-specific asparagine synthetase, type A; regenerating the plant from the cell; and growing the plant; whereby the growth of the plant is increased relative to non-transformed plants.

14. A method for increasing growth of a plant comprising: transforming a plant cell so that the cell contains DNA coding for *E. coli* ammonium-specific asparagine synthetase, type A, wherein the cell expresses *E. coli* ammonium-specific asparagine synthetase, type A; regenerating the plant from the cell; and growing the plant; whereby the growth of the plant is increased relative to non-transformed plants.

15. A method as claimed in claim 13 further comprising treating the plant with a glutamine synthetase inhibitor.

16. A method according to claim 15 wherein the glutamine synthetase inhibitor is phosphinothricine or methionine sulfoximine.

17. A method according to claim 16 wherein the glutamine synthetase inhibitor is phosphinothricine.

18. A method as claimed in claim 14 further comprising treating the plant with a glutamine synthetase inhibitor.

19. A method according to claim 18 wherein the glutamine synthetase inhibitor is phosphinothricine or methionine sulfoximine.

20. A method according to claim 19 wherein the glutamine synthetase inhibitor is phosphinothricine.

21. A method for increasing growth of a plant comprising: regenerating the plant from a cell as claimed in claim 1; and growing the plant; whereby the growth of the plant is increased relative to non-transformed plants.

22. A method as claimed in claim 21 further comprising treating the plant with a glutamine synthetase inhibitor.

23. A method according to claim 22 wherein the glutamine synthetase inhibitor is phosphinothricine or methionine sulfoximine.

24. A method according to claim 23 wherein the glutamine synthetase inhibitor is phosphinothricine.

\* \* \* \* \*